(12) United States Patent
Chelak et al.

(10) Patent No.: US 9,079,005 B2
(45) Date of Patent: Jul. 14, 2015

(54) SAMPLING PORT

(71) Applicant: NP Medical Inc., Clinton, MA (US)

(72) Inventors: Todd M. Chelak, Westborough, MA (US); Ian Kimball, Townsend, MA (US); Nicholas Dennis, Sterling, MA (US); Luis Maseda, Natick, MA (US)

(73) Assignee: NP Medical Inc., Clinton, MA (US)

( * ) Notice: Subject to any disclaimer, the term of this patent is extended or adjusted under 35 U.S.C. 154(b) by 0 days.

(21) Appl. No.: 14/093,937

(22) Filed: Dec. 2, 2013

(65) Prior Publication Data
US 2015/0112271 A1  Apr. 23, 2015

Related U.S. Application Data

(60) Provisional application No. 61/892,793, filed on Oct. 18, 2013.

(51) Int. Cl.
| *A61M 39/06* | (2006.01) |
| *A61M 39/04* | (2006.01) |
| *A61M 39/00* | (2006.01) |
| *A61M 39/26* | (2006.01) |
| *A61M 39/02* | (2006.01) |

(52) U.S. Cl.
CPC ............... *A61M 39/06* (2013.01); *A61M 39/04* (2013.01); *A61M 39/00* (2013.01); *A61M 39/26* (2013.01); *A61M 2039/0202* (2013.01)

(58) Field of Classification Search
CPC ..... A61M 39/02; A61M 39/10; A61M 39/22; A61M 2039/0202; A61M 2039/1077
USPC ........................................ 604/249, 256, 539
See application file for complete search history.

(56) References Cited

U.S. PATENT DOCUMENTS

| 4,936,542 A | 6/1990 | Beard ........................... 251/117 |
| 5,098,405 A | 3/1992 | Peterson et al. .............. 604/247 |
| 5,203,771 A | 4/1993 | Melker et al. .................... 604/53 |
| 5,221,271 A | 6/1993 | Nicholson et al. ............ 604/283 |

(Continued)

FOREIGN PATENT DOCUMENTS

| EP | 0 247 425 | 12/1987 | .............. A61M 5/14 |
| EP | 1 234 596 A1 | 8/2002 | ............ A61M 39/00 |
| WO | WO 2008/101025 | 8/2008 | ............... A61B 5/15 |

OTHER PUBLICATIONS

European Patent Office, International Search Report—Application No. PCT/US2014/058234, date of mailing Dec. 16, 20014, *including the Written Opinion of the International Searching Authority* (10 pages).

*Primary Examiner* — Laura Bouchelle
(74) *Attorney, Agent, or Firm* — Sunstein Kann Murphy & Timbers LLP

(57) ABSTRACT

A sampling port includes a hub having a body that forms a hub chamber for containing a fluid. The hub also has a proximal opening to the hub chamber for receiving a medical implement, and the hub chamber has a valve member that normally closes the opening. The valve member has a valve wall forming a valve interior. The sampling port also has a first and second fluid channel formed by the hub body and in fluid communication with the hub chamber. The first and second channels have radial portions and proximally extending portions with proximally extending longitudinal axes. The proximally extending longitudinal axes form a plane therebetween that diverges from the longitudinal axis of the first fluid channel.

26 Claims, 15 Drawing Sheets

(56) References Cited

U.S. PATENT DOCUMENTS

| | | | |
|---|---|---|---|
| 5,354,275 A | 10/1994 | Behnke et al. | 604/86 |
| 5,360,413 A | 11/1994 | Leason et al. | 604/249 |
| 5,417,673 A * | 5/1995 | Gordon | 604/539 |
| 6,089,541 A | 7/2000 | Weinheimer et al. | 251/149.6 |
| RE37,357 E | 9/2001 | Lynn | 604/533 |
| 7,314,061 B2 * | 1/2008 | Peppel | 137/605 |
| 7,556,060 B2 * | 7/2009 | Guala | 137/599.03 |
| 7,984,730 B2 | 7/2011 | Ziv et al. | 137/625.46 |
| 2005/0261637 A1 | 11/2005 | Miller | 604/256 |
| 2006/0213563 A1 | 9/2006 | Peppel | 137/605 |
| 2006/0217671 A1 | 9/2006 | Peppel | 604/246 |
| 2011/0308651 A1 | 12/2011 | Ziv et al. | 137/625.46 |

\* cited by examiner

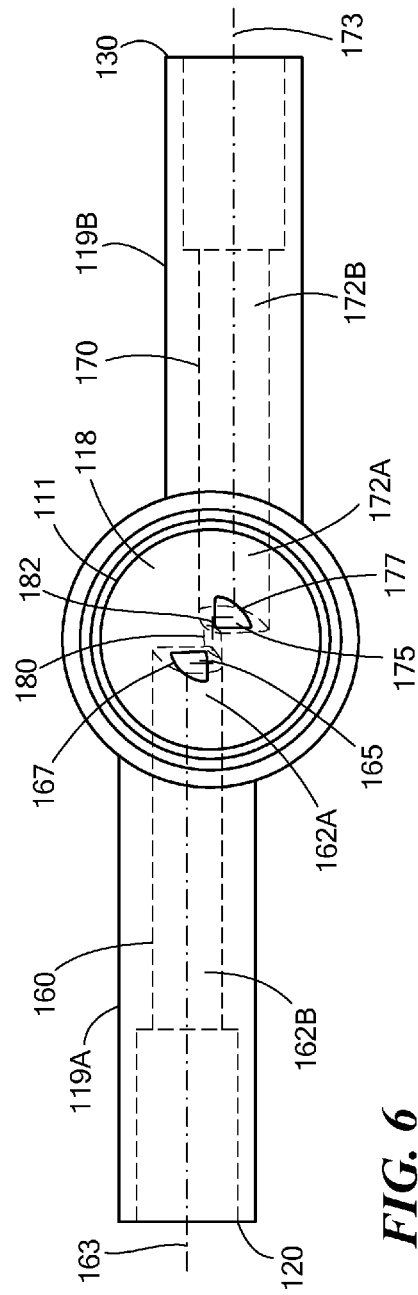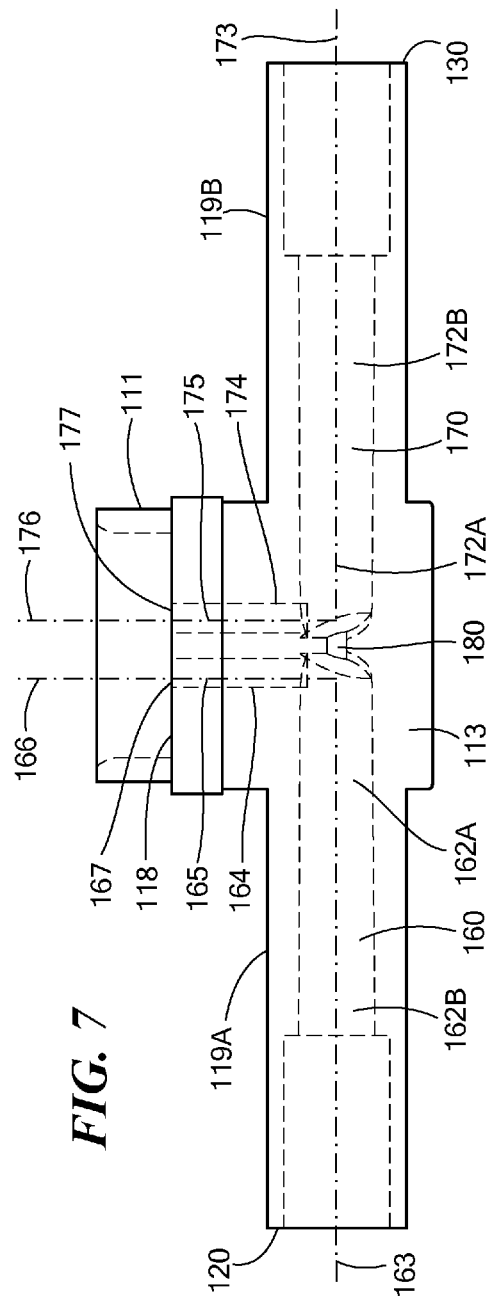

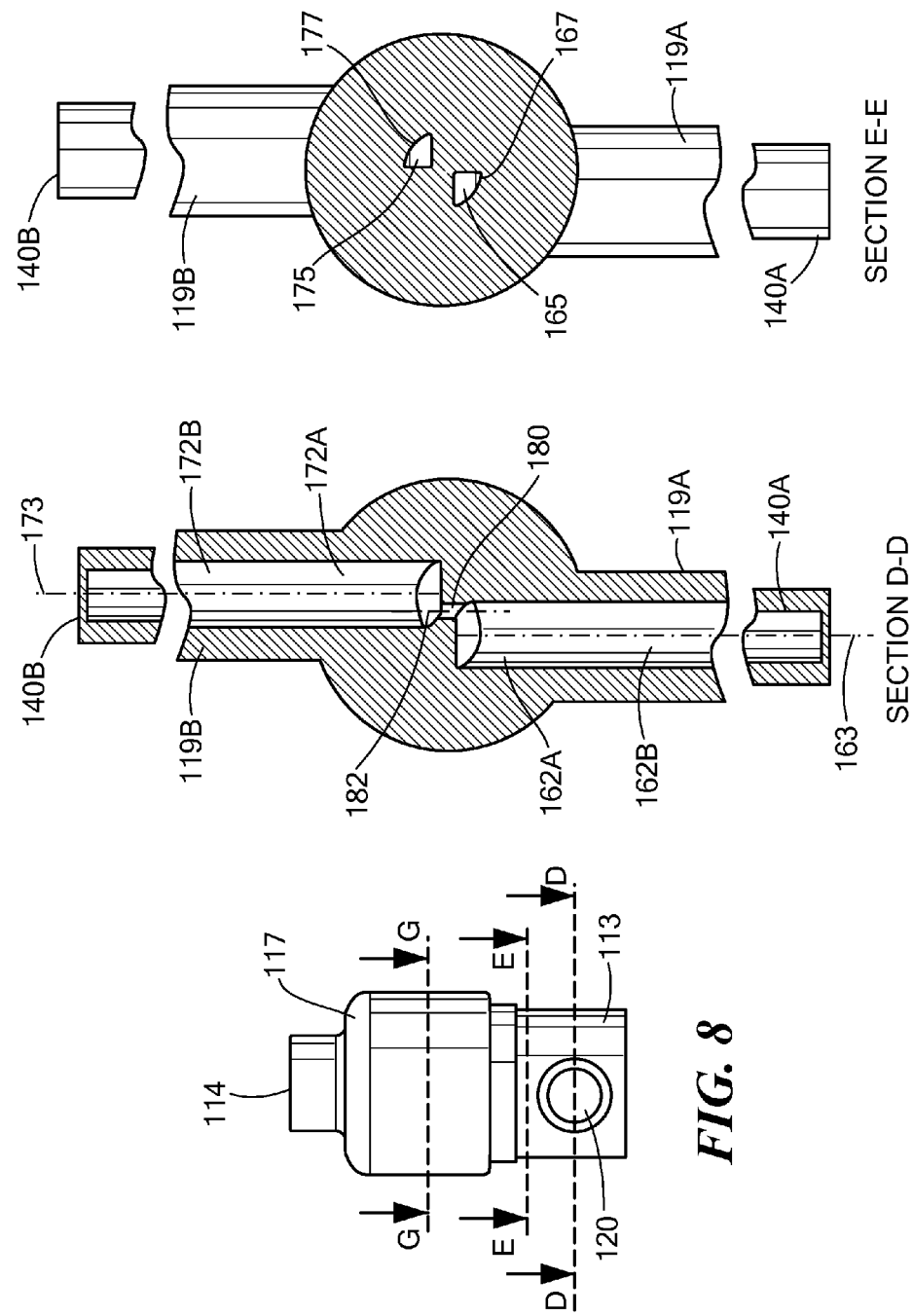

SECTION G-G

SAMPLING PORT

PRIORITY

This patent application claims priority from provisional U.S. patent application No. 61/892,793, filed Oct. 18, 2013 entitled, "SAMPLE PORT," and naming Todd Chelak, Ian Kimball, and Nicholas Dennis as inventors, the disclosure of which is incorporated herein, in its entirety, by reference.

FIELD OF THE INVENTION

Various embodiments of the invention generally relate to fluid delivery devices and, more particularly, various embodiments of the invention relate to sample ports within arterial or venous fluid transfer sets.

BACKGROUND OF THE INVENTION

There are a number of fluid transfer applications (e.g., applications in which fluid is being administered to and/or drawn from a patient) that require a medical practitioner to take a sample of the blood being drawn from the patient and/or the fluid being transferred to the patient. In such applications, the fluid transfer set may include a sample port that allows the medical practitioner to draw a sample of the blood or fluid without removing the catheter from the patient or otherwise disconnecting the components of the fluid transfer set. Additionally, the sampling port may be used to directly deliver a fluid to the patient by connection of a syringe, a secondary transfer set, and/or other fluid delivery devices known in the field.

Furthermore, in some critical care applications, the medical practitioner may be required to regularly monitor the patient's arterial blood pressure. In such applications, the fluid transfer set may include a pressure transducer that connects to a display that graphically shows a read-out of the arterial blood pressure. In some prior art fluid transfer sets, the sampling ports can negatively interfere with the blood pressure signal from the pressure transducer. Additionally, some prior art sampling ports utilize stop-cocks, which require substantial manipulation from the medical practitioner during use.

SUMMARY OF VARIOUS EMBODIMENTS

In accordance with one embodiment of the invention, a sampling port includes a hub having a body forming a hub chamber for containing a fluid. The hub further includes a proximal opening to the hub chamber for receiving a medical implement. The hub chamber may have a valve member that normally closes the opening and has a valve wall that forms a valve interior.

The sampling port may also include a first and second fluid channel formed by the hub body. The first fluid channel may be in fluid communication with the hub chamber, and may have a first radial portion and a first proximally extending portion. The first radial portion may have a first radial longitudinal axis, and the first proximally extending portion may have a first proximally extending flow path with a first proximally extending longitudinal axis. The second fluid channel may also be in fluid communication with the hub chamber, and may have a second radial portion and a second proximally extending portion. The second radial portion may have a second radial longitudinal axis, and the second proximally extending portion may have a second proximally extending flow path with a second proximally extending longitudinal axis. The first and second proximally extending longitudinal axes may form a plane therebetween that diverges from the first radial longitudinal axis.

In some embodiments, the first proximally extending flow path may have a first cross-sectional shape, and the second proximally extending flow path may have a second cross-sectional shape. The first and second cross-sectional shapes may be the same and/or the first cross sectional shape may be oriented about 180 degrees relative to the second cross-sectional shape.

In accordance with further embodiments, the first proximally extending flow path may be aligned with and generally orthogonal to the first radial longitudinal axis. The first and second proximally extending portions may also extend into the valve interior, and the hub may be free of a stop-cock valve. Additionally or alternatively, the first radial longitudinal axis may be generally parallel with and spaced from the second radial longitudinal axis, and/or the first radial longitudinal axis and second radial longitudinal axis may diverge.

The valve wall may form a distal port for the valve interior, and the first proximally extending portion may have a proximally facing port. The distal port of the valve may be more proximal than the proximally facing port, or the distal port may share the same plane as the proximally facing port. The first and second proximally extending portions may be completely unmovable relative to the hub. The valve member may be or have an elastomeric member with a proximal, swabbable portion.

In still further embodiments, the hub body may include a distal portion, and the hub chamber may be proximal to the distal portion. The distal portion may form the first proximally extending portion and the second proximally extending portion. The first proximally extending portion may terminate at a first proximally facing port, and the second proximally extending portion may terminate at a second proximally facing port. The first and second proximally facing ports may terminate at the boundary of the hub chamber.

The sampling port may also include a bypass channel with a bypass longitudinal axis. The bypass channel may directly fluidly connect the first radial portion and the second radial portion, and the bypass longitudinal axis may be substantially parallel with the first radial longitudinal axis, and/or the second radial longitudinal axis.

In accordance with additional embodiments, a sampling port may include a hub having a body forming a hub chamber for containing a fluid. The hub may also have a proximal opening to the hub chamber for receiving a medical implement, and the hub chamber may have a valve member normally closing the opening. The sampling port may also have a first fluid channel and a second fluid channel formed by the hub body and in fluid communication with the hub chamber. The first fluid channel may have a first radial portion and a first proximally extending portion. The first radial portion may have a first longitudinal axis. The second fluid channel may have a second radial portion and a second proximally extending portion. The second radial portion may have a second longitudinal axis. The first longitudinal axis may be generally parallel with and spaced from the second longitudinal axis. The first radial portion may include a first interior radial portion within the hub chamber and a first exterior radial portion outside of the hub chamber.

In some embodiments, the first longitudinal axis and the second longitudinal axis may diverge, and/or the first longitudinal axis and the second longitudinal axis may be substantially parallel and spaced apart. Additionally or alternatively, the first proximally extending portion may be substantially orthogonal to the first longitudinal axis and/or the second proximally extending portion may be substantially orthogonal to the second longitudinal axis.

In further embodiments, the first proximally extending portion may include a first proximally facing fluid port, and the second proximally extending portion may include a second proximally facing fluid port. The first proximally extending portion may be spaced from and/or aligned with the first longitudinal axis. The first and second proximally extending portions may oppose each other at an angle to the first longitudinal axis.

The valve member may include an elastomeric member having a proximal, swabbable portion. Additionally or alternatively, the valve member may include a normally closed proximal opening and a valve wall forming a valve interior. The first and/or second proximally extending portions may extend into the valve interior, and may have proximally facing port(s) that is/are configured to direct fluid into the valve interior.

In further embodiments, the sampling port may include a bypass channel with a bypass longitudinal axis. The bypass channel may directly fluidly connect the first radial portion and the second radial portion. The bypass longitudinal axis may be substantially parallel with the first longitudinal axis and/or the second longitudinal axis. In some embodiments, the bypass longitudinal axis may be spaced from the first longitudinal axis.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 6 schematically shows a top view of the sampling port shown in FIG. 1 with the valve member removed, in accordance with some embodiments of the present invention.

FIG. 7 schematically shows a side view of the sampling port shown in FIG. 1 with the valve member removed in accordance with some embodiments of the present invention.

FIG. 8 schematically shows an end view of the sampling port shown in FIG. 1 in accordance with some embodiments of the present invention.

FIG. 9 schematically shows a cross sectional top view of the sampling port shown in FIG. 8 along line D-D, in accordance with some embodiments of the present invention.

FIG. 10 schematically shows a cross sectional top view of the sampling port shown in FIG. 8 along line E-E, in accordance with some embodiments of the present invention.

DESCRIPTION OF ILLUSTRATIVE EMBODIMENTS

In illustrative embodiments, a sampling port has a simpler design but does not sacrifice its ability to adequately flush its interior. To that end, the sampling port has a hub with offset fluid channels extending into its interior. This offset channel configuration and open interior cooperate to direct flushing fluid (e.g., saline) proximally toward normally difficult to reach regions, consequently delivering enhanced flushing. Details of illustrative embodiments are discussed below.

Figure 1:
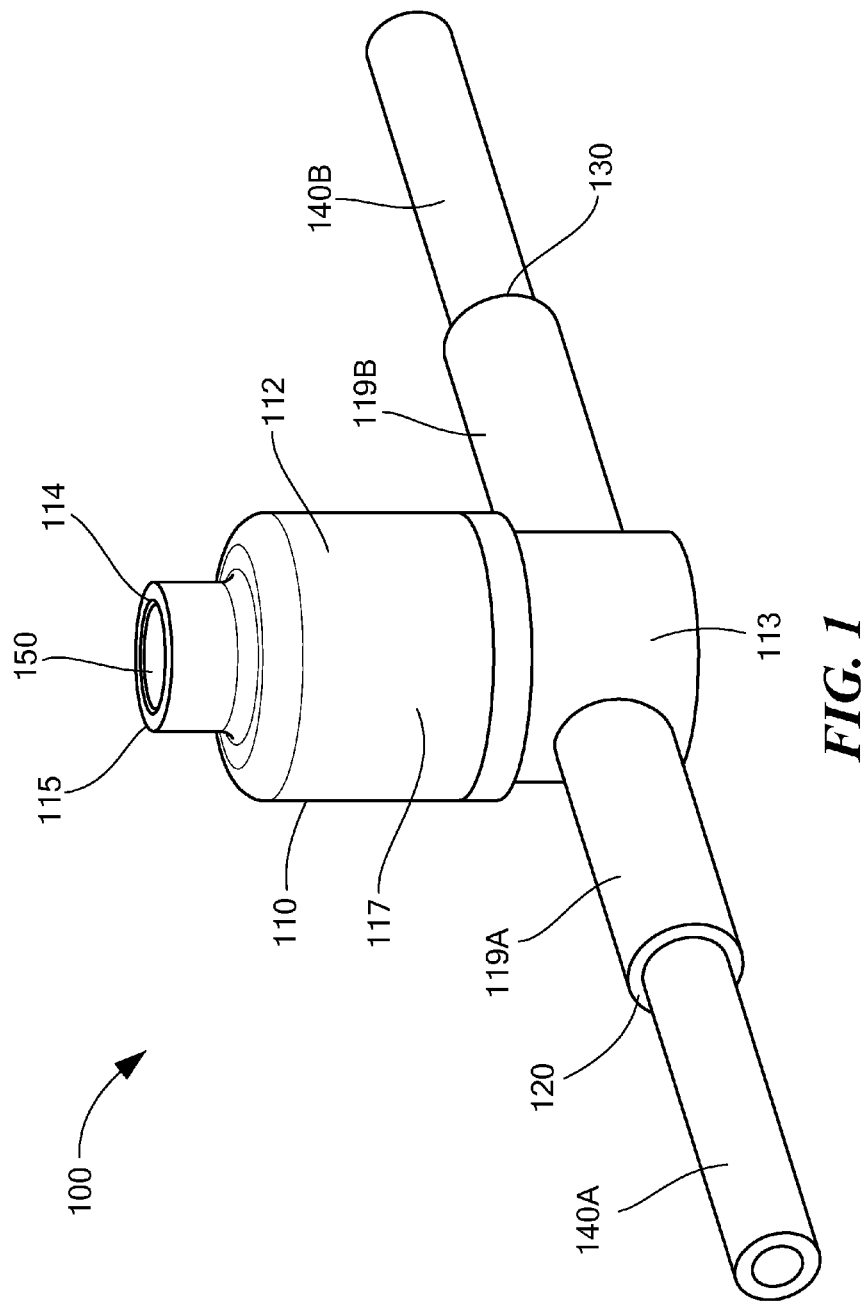
FIG. 1 schematically shows a perspective view of a sampling port in accordance with various embodiments of the present invention.

FIG. 1 schematically shows a perspective view of a sampling port 100 configured in accordance with illustrative embodiments of the invention. The sampling port 100 includes a hub portion 110 with an inlet 120 and outlet 130 extending out from the body 112 of the hub portion 110. The inlet 120 and outlet 130 may each be connected to a section of tubing 140A/B. For example, the sampling port 100 may be part of a fluid transfer set used to transfer fluids to a patient and/or draw blood from the patient. To that end, the inlet 120 may be connected (e.g., welded, glued, press-fit, etc.) to a section of tubing 140A that leads to a drip chamber and a fluid bag (e.g., containing medicine or other fluid being intravenously supplied to a patient). Conversely, the outlet 130 may be connected to a section of tubing 140B that leads to a catheter or needle inserted into the patient (not shown).

In addition to the fluid bag, in some applications (e.g., in critical care applications), it may be necessary to monitor the arterial pressure of the patient (e.g., the intra-arterial blood pressure at the insertion site of the catheter). Therefore, in some instances, the fluid transfer set may also include a pressure transducer (not shown) with a strain gauge that measures the pressure within the artery, converts it into an electrical signal, and forwards the signal to a monitor that plugs into the transducer. The monitor, in turn, may display a graphic representing the intra-arterial blood pressure of the patient.

Figure 2:
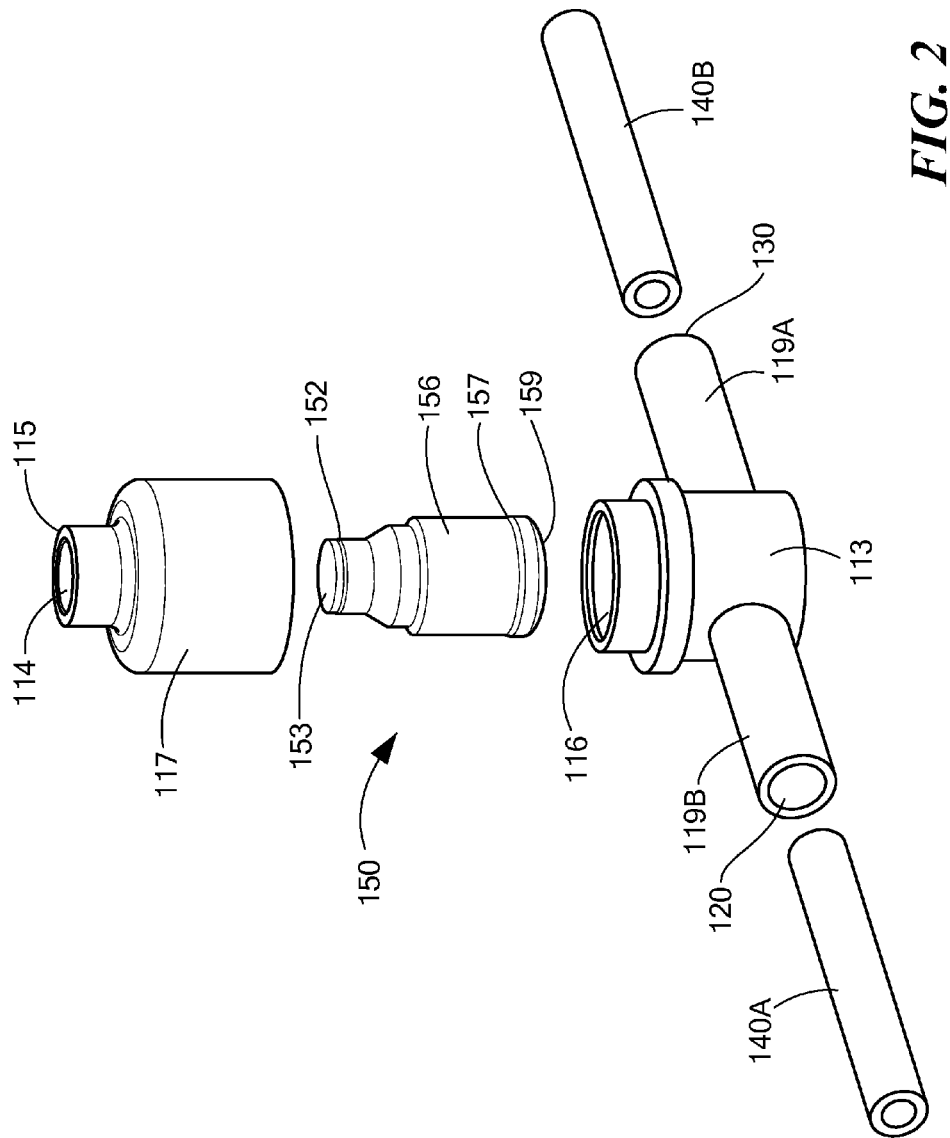
FIG. 2 schematically shows an exploded view of the sampling port shown in FIG. 1, in accordance with illustrative embodiments of the present invention.
Figure 3:
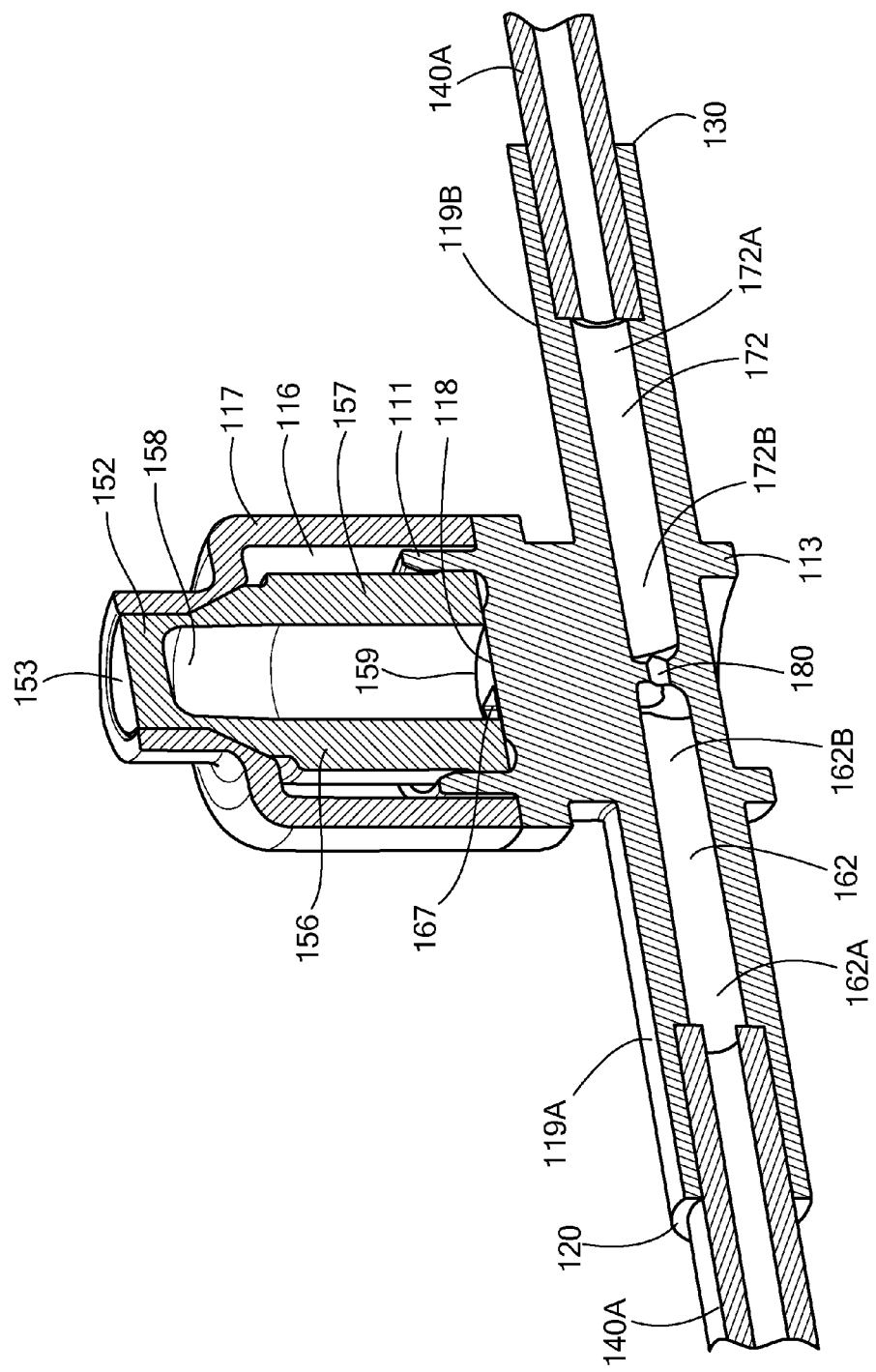
FIG. 3 schematically shows a perspective cross-sectional view of the sampling port shown in FIG. 1, in accordance with illustrative embodiments of the present invention FIG. 4 schematically shows a side view of the sampling port shown FIG. 1, in accordance with various embodiments of the present invention.
Figure 4:
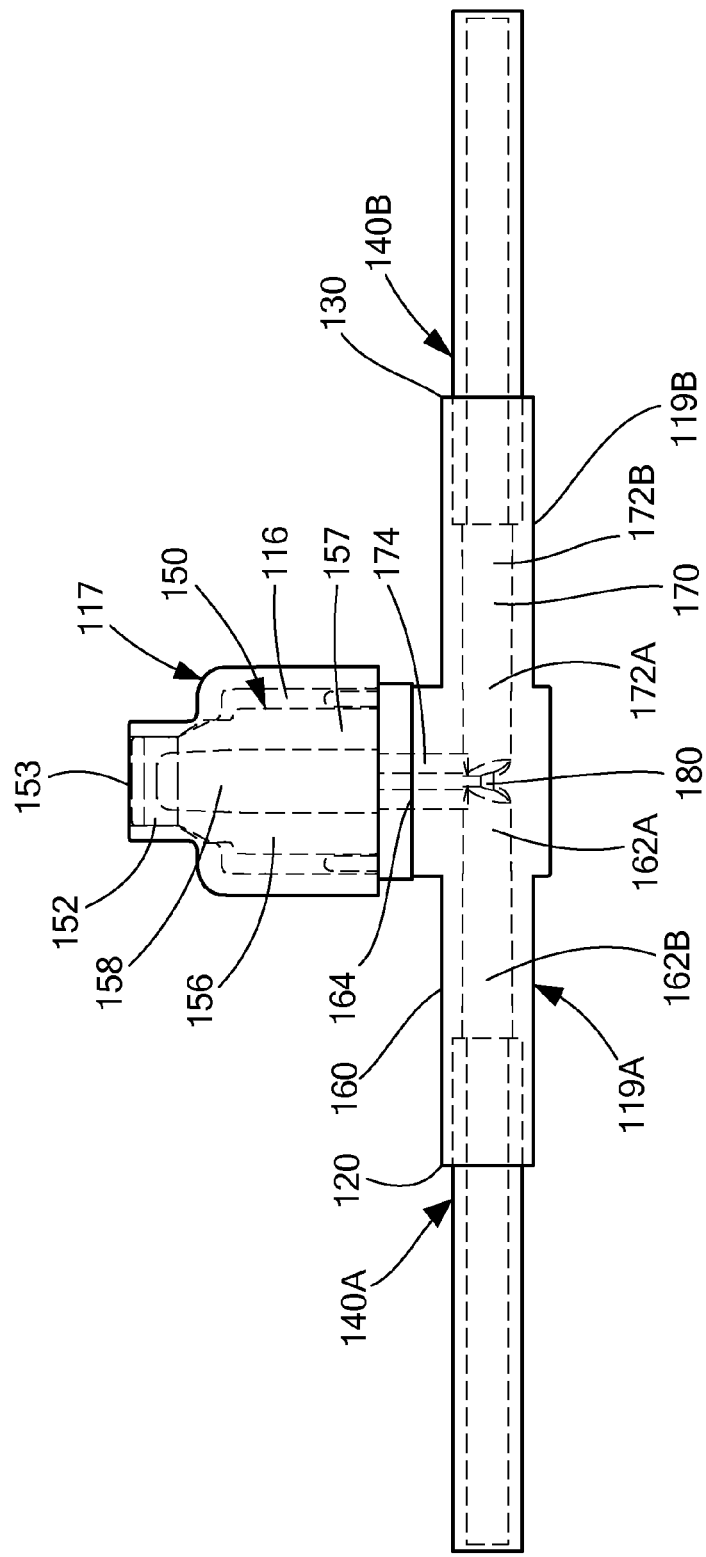
Figure 5:
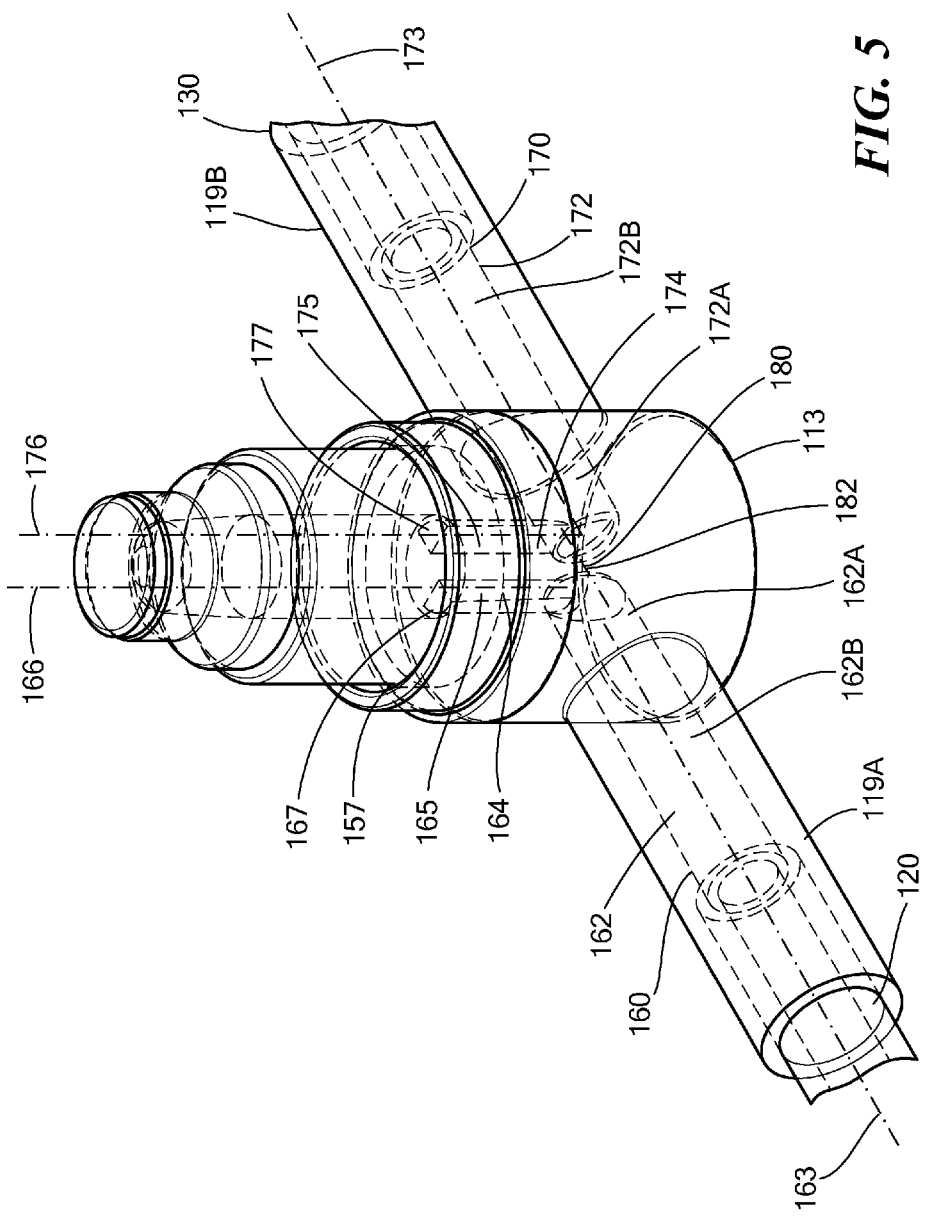
FIG. 5 schematically shows a perspective view of the sampling port shown in FIG. 1 with the fluid paths visible, in accordance with illustrative embodiments of the present invention.
Figure 11:
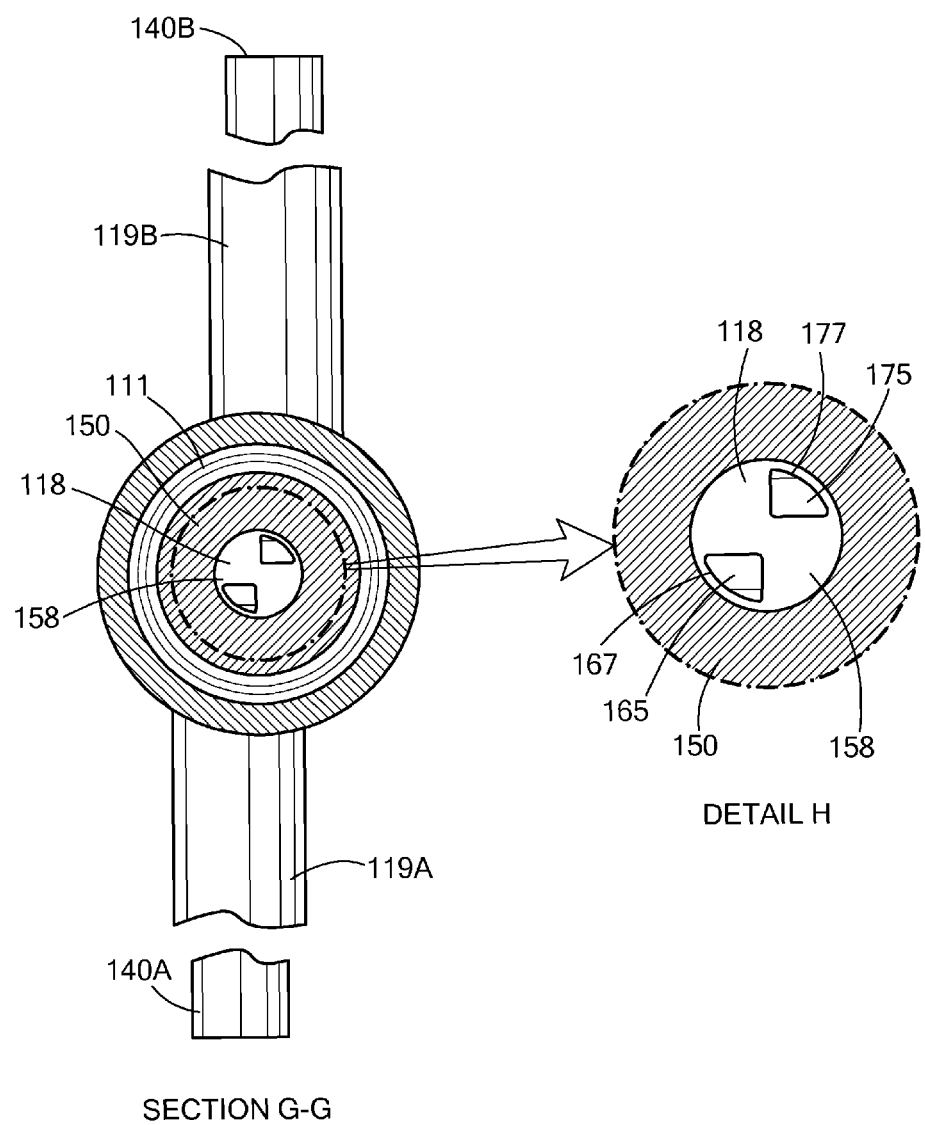
FIG. 11 schematically shows a cross sectional top view of the sampling port shown in FIG. 8 along line G-G, in accordance with some embodiments of the present invention.

As best shown in FIGS. 2 and 3, the body 112 of the hub 110 may include a distal portion 113 and a proximal portion 117 that, when secured together, form a hub chamber 116 within the interior of the body 112 (e.g., within the interior of the proximal portion 117). To take a sample, the sampling port 100 may also include a proximal opening 114 within the hub 110 (e.g., within the proximal portion 117 of the body 112) capable of receiving a medical implement (e.g., a Luer, needleless syringe, blunt cannula, etc.) that can be used to draw a sample from the sampling port 100. The sampling port 100 also has an elastomeric valve member 150 within the hub chamber 116 to seal the proximal opening 114.

The valve member 150 may include a proximal portion 152 and a valve wall 156 that extends distally from the proximal portion 152 within the hub chamber 116. As shown in FIG. 3, the valve wall 156 forms a valve interior 158 within the hub chamber 116. The valve member 150 also has a distal end 157 that preferably is open to form a distal port 159 into the valve interior 158. To help support the valve member 150 within the hub chamber 116, the hub body 112 has a proximally extending annular wall 111 that essentially creates a recess within the hub chamber 116 (e.g., within the distal portion 113 of the body 112). The valve member 150 (e.g., the valve wall 156) may reside within the recess and rest on a proximally facing surface 118 on the distal portion 113 of the body 112. As discussed in greater detail below, as fluid flows through the sampling port 100, the fluid (e.g., medication, saline, blood, etc.) flows into and out of the valve interior 158 via the distal port 159.

In some embodiments, the proximal portion 152 of the valve member 150 may be flush with or extend slightly above an exterior proximal opening face 115 of the proximal opening 114 (FIGS. 1 and 3) of the hub 110. The proximal portion 152 of the valve member 150 and the exterior inlet face 115 thus present a swabbable surface, i.e., it may be easily wiped clean with an alcohol swab, for example, or other swab.

As mentioned above, the proximal opening 114 is configured to draw a sample from the valve interior 158. To that end, the valve member 150 includes a resealable aperture 153 extending through the proximal portion 152. Among other things, the aperture 153 may be a pierced hole or a slit. Alternatively, the proximal portion 152 may be molded with the aperture 153. When the valve member 150 is in a closed mode (i.e., preventing passage of fluid), as shown in FIGS. 1 and 3, the aperture 153 may be held closed by the inner surface of the proximal opening 114. In that case, the inner diameter of the proximal opening may be smaller than the outer diameter of the proximal portion 152 and thus, the hub body 112 (e.g., the portion near the proximal opening 114) squeezes the aperture 153 closed. Alternatively, the valve member 150 (e.g., the proximal portion 152) may be formed so that the aperture 153 normally stays closed in the absence of radially inward force provided by the inner diameter of the proximal opening 114. In other words, the proximal portion 152 may be formed so that the aperture 153 normally is closed.

During operation (e.g., when taking a sample from the fluid transfer set), the medical practitioner may insert the medical implement into the proximal opening 114 of the hub 110. As the medical implement is inserted, the valve member 150, which normally closes the proximal opening 114, moves/deforms distally within the hub chamber 116. As the valve member 150 continues to move/deform distally into the hub chamber 116, the aperture 153 will open (e.g., when the proximal portion 152 enters the larger inner diameter portion of the proximal portion 117 of the body 112) to create fluid communication between the medical implement and the valve interior 158. Conversely, when the medical implement is withdrawn from the proximal opening 114 (e.g., after sampling is complete), the elastomeric properties of the valve member 150 cause the valve member 150 to begin to move proximally within the hub chamber 116 and return to its at-rest position with the proximal portion 152 within (and closing) the proximal opening 114.

As shown in FIGS. 4-7, the sampling port 100 has a plurality of fluid channels extending through the hub body 112 that allow 1) fluid to flow through the sampling port 100 and 2) the sample to be taken through the proximal opening 114. For example, the hub body 112 may form a first fluid channel 160 and a second fluid channel 170. The first fluid channel 160 fluidly connects the inlet 120 and the valve interior 158. Similarly, the second fluid channel 170 fluidly connects the valve interior 158 and the outlet 130. In this manner, when primed, fluid flowing through the sampling port 100 flows into the inlet 120, through the first fluid channel 160, into the valve interior 158, and out of the sampling port 100 through the second fluid channel 170 and outlet 130. Similarly, fluid may flow through the plurality of fluid channels of the sampling port 100 in the opposite direction.

Both the first fluid channel 160 and the second fluid channel 170 have a radial portion extending radially inwardly, and a proximally extending portion extending proximally toward the valve interior 158. For example, as also shown in FIGS. 4-7, the first fluid channel 160 has a first radial portion 162 that extends radially outward from the hub body 112 toward the inlet 120 (e.g., along a first radial longitudinal axis 163), and a first proximally extending portion 164 that extends proximally from the first radial portion 162 toward the valve interior 158 (e.g., along a first proximally extending longitudinal axis 166). In a corresponding manner, the second fluid channel 170 has a second radial portion 172 that extends radially outward from the hub body 112 toward the outlet 130 (e.g., along a second radial longitudinal axis 173), and a second proximally extending portion 174 that extends proximally from the second radial portion 172 toward the valve interior 158 (e.g., along a second proximally extending longitudinal axis 176). The proximally extending portions 164/174 may define proximally extending flow paths 165/175.

The longitudinal axes 163 and 173 are generally straight and with a vector direction. In illustrative embodiments, these axes 163 and 173 may be in the centroid of the cross-sectional shape of the respective portions, or close to the centroid. For example, if the cross-sectional shape is a circle, then the axis preferably is along the center of the circle. If the cross-sectional shape is irregular, then the longitudinal axis preferably is considered to be at the centroid of the cross-sectional shape. In alternative embodiments, the longitudinal axes 163 and 173 are not necessarily at the centroid of their cross-sectional channel shapes. In either of those cases, the longitudinal axis are considered to be generally straight. The radial portions 162/172, in turn, are considered to have two portions—interior radial portions 162A/172A that are located within the hub chamber 116 and exterior radial portions 162B/172B that are located outside of the hub chamber 116. For example, the hub body 112 can have projections 119A/119B that extend outward to form the exterior radial portions 162B/172B. In such embodiments, the projections 119A/119B respectively may terminate at the inlet 120 and the outlet 130. Additionally, although the projections 119A/119B are shown as being integral to the hub body 112, in some embodiments, the projections 119A/119B may be separate components that are secured to the hub body 112 (e.g., by gluing, welding, etc. the projections 119A/119B to the portion of the hub body 112 forming the chamber 116).

Like the radially extending portions 162/172 (in particular, the interior radial portions 162A/172A), the proximally extending portions 164/174 may be formed by the hub body 112 (e.g., the distal portion 113 of the hub 110), such that the proximally extending portions 164/174 are not moveable relative to the remainder of the hub 110. Additionally, as best shown in FIGS. 6 and 7, the first proximally extending portion 164 is aligned with and/or generally orthogonal to the first radial longitudinal axis 163. Similarly, the second proximally extending portion 174 is aligned with and/or generally orthogonal to the second radial longitudinal axis 173. In other words, a distal projection of the first proximally extending flow path 165 (i.e., if it continued distally toward the first proximally extending flow path 165) intersects the first radial longitudinal axis 163. The second proximally extending flow path 175 also has a similar relationship to the second radial longitudinal axis 173.

It should be noted that, in other embodiments, the proximally extending portions 164/174 need not be orthogonal to the radial longitudinal axes 163/173. For example, in some embodiments, one or both of the proximally extending portions 164/174 may not be oriented at a right angle with respect to the radial longitudinal axes 163/173. Instead, the proximally extending portions 164/174 can be oriented at an angle greater than or less than 90 degrees with respect to the radial longitudinal axes 163/173

Each of the proximally extending portions 164/174 can include a proximally facing fluid port 167/177, for example, at the ends of the flow paths 165/175 formed by the proximally extending portions 164/174. As shown in the figures (e.g., FIGS. 5, 6, and 7), the fluid ports 167/177 may be formed within the proximally facing surface 118 of the hub body 112 such that they are located just distal to the distal port 159 of the valve member 150 and/or share the same plane as the distal port 159 (e.g., because the distal end 157 of the valve member 150 may rest on the proximal facing surface 118). Alternatively, in some embodiments, one or both of the proximally extending portions 164/174 may extend into the valve interior 158 such that one or both of the proximally facing ports 167/177 are located within the valve interior 158 (e.g., proximal to the distal port 159 of the valve member 150).

In some embodiments, the first fluid channel 160 and the second fluid channel 170 are offset from one another. To that end, in some embodiments, the first and second longitudinal axes 163 and 173 are spaced apart. For example, those axes 163 and 173 may be generally parallel but spaced apart. In the embodiment shown in FIG. 6, for example, the channels 162 and 172 are 180 degrees opposed across the hub 110, but their axes 163 and 173 are parallel and spaced apart. In other embodiments, however, those axes 163 and 173 may diverge (i.e., they intersect if they are projected toward infinity).

The proximally extending portions 164/174 also may contribute to the offset nature of the channels 160 and 170. Specifically, in a manner similar to the radial portions 162/172, the proximally extending portions 164/174 also are considered to have longitudinal axes 166/176. These two axes, which can be in some off-centroid location or in a centroid location of the portions 164/174, often are spaced apart and often generally parallel. In illustrative embodiments, these axes 166 and 176 form a plane that intersects either or both of the longitudinal axes 163 and 173 of the radial portions 162 and 172. In other embodiments, this plane is generally parallel with either or both the axes 163 and 173. In that latter case, this plane may be between the axes 163 and 173.

As also shown in FIGS. 6 and 9-11, the proximally extending flow paths 165/175 formed by the proximally extending portions 164/174 of the fluid channels 160/170 may have identical cross-sectional shapes. Their cross-sectional shapes, however, may be oriented/rotated about 180 degrees with respect to one another. For example, if the cross-sectional shapes of the proximally extending flow paths 165/175 are pie-shaped, then the flow paths 165/175 may be oriented such that the pointed portions of the cross-sectional shapes face each other.

It is important to note that, although, the cross-sectional shapes are described above as being oriented about 180 degrees with respect to one another, some embodiments may orient them differently. For example, in some embodiments, the flow paths 165/175 (e.g., the cross-sectional shapes of the flow paths 165/175) may be oriented more or less than 180 degrees relative to one another. Additionally, it is also important to note that the cross-sectional shapes need not be pie shaped, and they need not be identical. For example, the cross-sectional shape of one of the proximally extending flow paths may be circular, and the cross-sectional shape of the other flow path may be semi-circular, elliptical, rectangular, square, etc. Furthermore, the cross-sectional areas of flow paths 165/175 may vary along the proximally extending portions 164/174. It should also be noted that the cross-sectional areas of flow paths 165/175 may be the same or different to achieve various flow patterns within the valve interior 158, for example, while the transfer set is being flushed with fluid from a fluid bag.

As mentioned above, some embodiments of the sampling port 100 described herein may be used in applications requiring continuous and real time monitoring of a patient's intra-arterial pressure. Certain monitoring systems, in turn, may benefit from a generally linear flow path through the sampling port 100 to maintain a pressure column. To that end, as shown in FIGS. 3-7 and 9, some embodiments of the sampling port 100 can include a bypass channel 180 that extends between and fluidly connects the first fluid channel 160 and the second fluid channel 170 to help maintain an unobstructed pressure column through the sampling port 100.

The bypass channel 180 (FIG. 6) may be parallel with the first fluid channel 160 and/or the second fluid channel 170. For example, the bypass channel 180 can extend along a bypass channel longitudinal axis 182 (FIGS. 6 and 9) that is parallel with and, perhaps, spaced from the first radial longitudinal axis 163 and/or the second radial longitudinal axis 173. Additionally, it should be noted that, to maintain the unobstructed pressure column, the bypass channel 180 need not have the same diameter or cross-sectional area as the first and second fluid channels 160/170. Therefore, in some embodiments, the diameter of the bypass channel 180, if it were circular in shape, may be smaller than that of the first and second fluid channels 160/170 (e.g., smaller than the radially extending portions 162/172). Furthermore, the cross-sectional area of the bypass channel 180 may vary along its length. It should also be noted that the cross-sectional area of the bypass channel 180 may be increased or decreased to achieve various flow patterns within the valve interior 158, such as while the transfer set is being flushed with fluid from a fluid bag.

Figure 12:
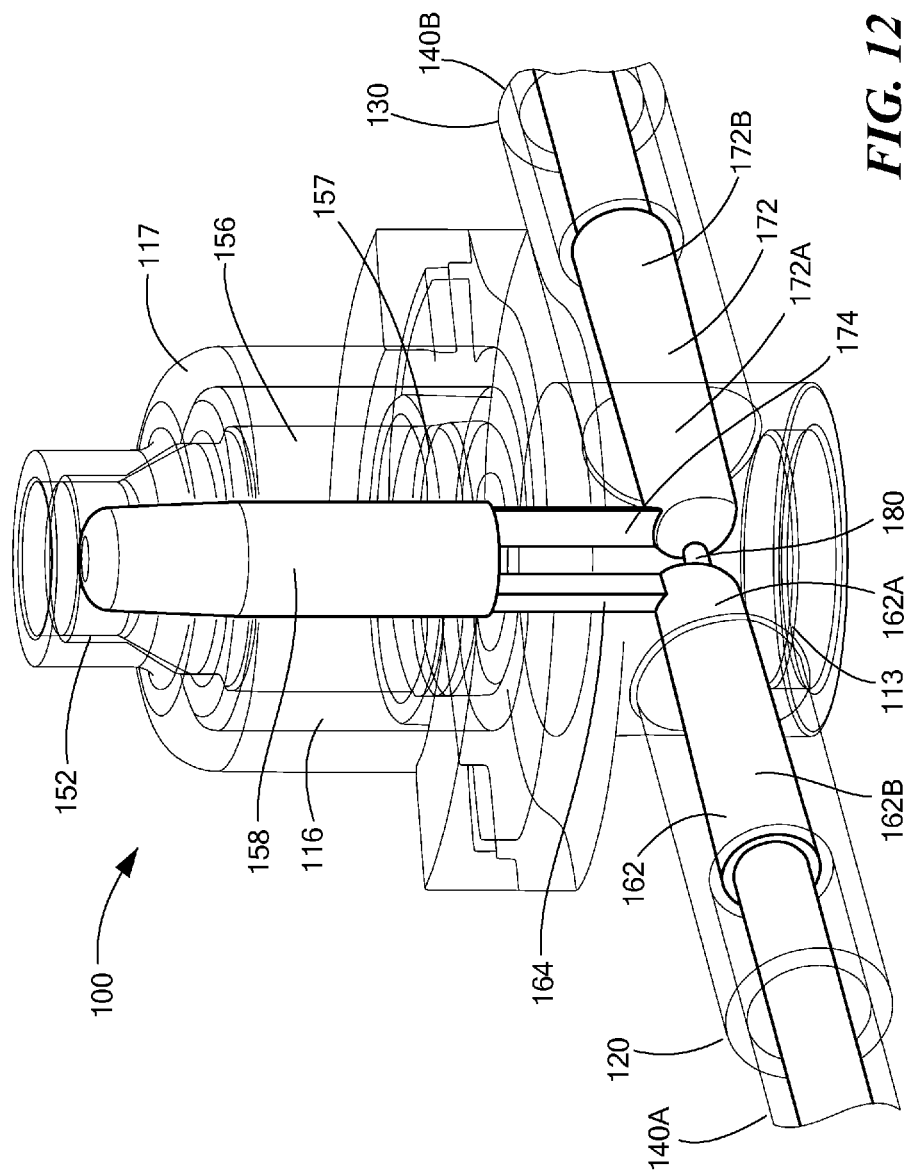
FIG. 12 schematically shows the fluid path through the sampling port shown in FIG. 1, in accordance with various embodiments of the present invention.

FIG. 12 shows the flow of fluid through the sampling port 100 as fluid is transferred to the patient and/or blood is being drawn from the patient. In particular, as fluid is being transferred to the patient (e.g., from a fluid bag), the fluid will enter the sampling port 100 through the tubing 140A connected to the fluid bag. The fluid will then flow through the first radial portion 162 (e.g., outer portion 162B and inner portion 162A) of the first fluid channel 160. As the fluid approaches the end of the inner portion 162A, the first proximally extending portion 164 (e.g., the first proximally extending flow path 165) will redirect the fluid proximally toward the proximal opening 114, where the fluid will substantially fill the interior 158 of the valve member 150 and reach the bottom of the proximal portion 152 of the valve member 150. The fluid will then exit the valve interior 158 through the second proximally extending portion 174 of the second fluid channel 170 (e.g., the second proximally extending flow path 175) and will exit the sampling port 100 through the second radial portion 172 and the outlet 130.

Conversely, if blood is to be drawn from the patient and through the sampling port 100, the flow through the sampling port 100 will be the opposite to that described above. For example, the blood will enter the sampling port 100 through tubing 140B connected to the patient (e.g., a catheter in the patient). The blood will then flow through the outer portion 172B of the second radial portion 172 and into the inner portion 172A of the second radial portion 172. As the fluid approaches the end of the inner portion 172A, the second proximally extending portion 174 (e.g., the second proximally extending flow path 175) will redirect the fluid proximally toward the proximal opening 114, where the fluid will substantially fill the interior 158 of the valve member 150 and reach the bottom of the proximal portion 152 of the valve member 150. The fluid will then exit the valve interior 158 through the first proximally extending portion 164 of the first fluid channel 160 (e.g., the first proximally extending flow path 165) and will exit the sampling port 100 through the first radial portion 162.

It is important to note that, in some embodiments, some fluid may pass through the bypass channel 180 as it flows through the sampling port 100. However, it is also important to note that the bypass channel 180 should be sized such that sufficient fluid is directed through the proximally extending portion 164 (or the proximally extending portion 174) to substantially fill the interior 158 of the valve. This will help ensure that the sampling port 100 is self-flushing.

Accordingly, after fluid is flowing through the sampling port 100 and has substantially filled the interior 158 of the valve 150 (e.g., after the system is primed as shown in FIG. 12), the medical practitioner may insert a medical implement into the proximal opening 114. As discussed above, this will deform the valve member 150 and cause the aperture 153 to open which, in turn, allows the medical practitioner to take a sample using the medical implement. Upon withdrawal of the medical implement, the elastomeric properties of the valve member 150 will cause the valve member 150 to close the proximal opening 114 and prevent fluid from escaping from the sampling port 100.

In addition to taking samples of the fluid passing through the sampling port 100, various embodiments of the present invention may be used to perform other important functions. For example, the medical practitioner may use the sampling port 100 to introduce fluids into the line. In such instances, if the medical practitioner needs to add a fluid to the fluid set (e.g., a dose of medication, etc.), the medical practitioner may connect the medical implement to the proximal opening 114 which, as discussed above, will cause the valve member 150 to open. Once the valve member 150 is open, the medical practitioner may then introduce the fluid/medicine into the sampling port 100, where it will mix with the fluid passing through the sampling port and be carried to the patient or fluid bag (depending on the direction of flow through the sampling port 100).

Additionally, some embodiments may be used to help prime the fluid set. For example, as the fluid set is being primed (e.g., preparing the fluid set for use by filling the tubing and various flow paths of the fluid set with fluid) air may become trapped within the fluid set. To remove this trapped air, the medical practitioner may connect a medical implement (e.g., a syringe or similar device) to the proximal opening 114 and draw the trapped air out of the fluid set and sampling port 100. This will ensure that the fluid set is properly primed and no air is trapped (which can negatively impact and/or prevent pressure measurements) in the system prior to use.

Figure 13A:
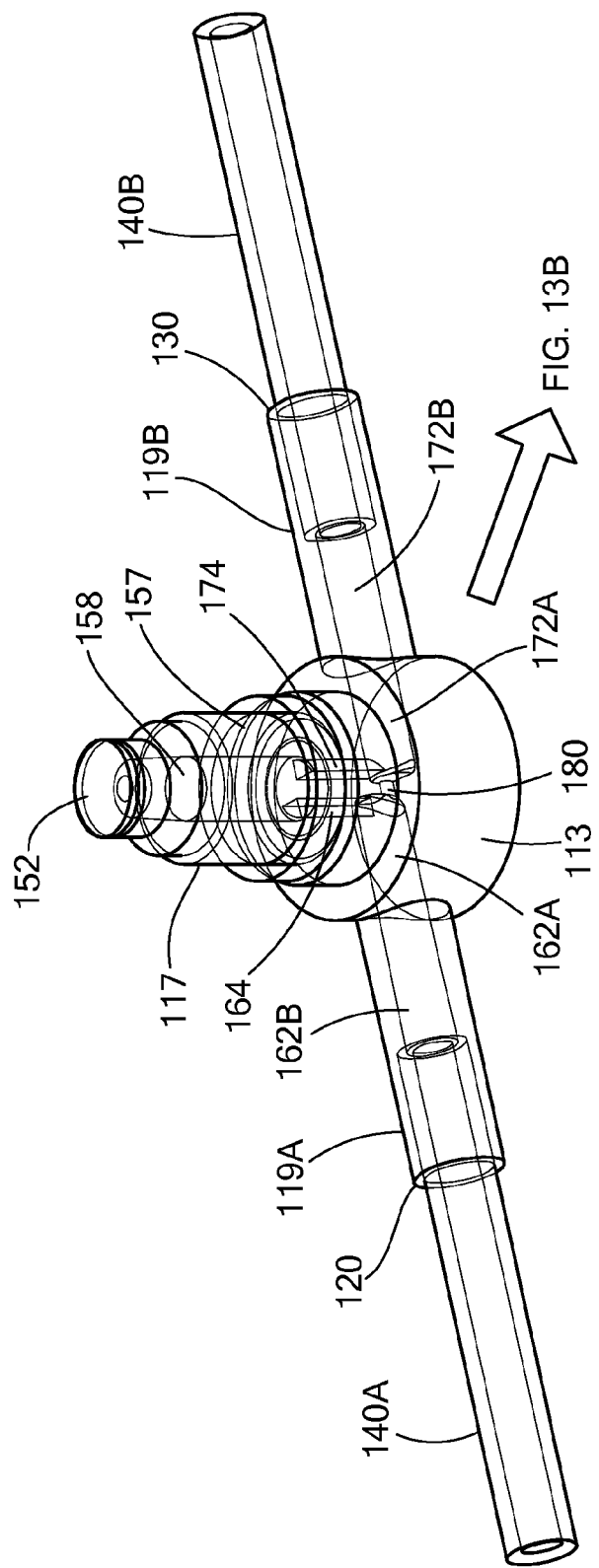
FIG. 13A schematically shows a perspective view of an alternative sampling port with the proximal portion of the hub removed, in accordance with additional embodiments of the present invention.
Figure 13B:
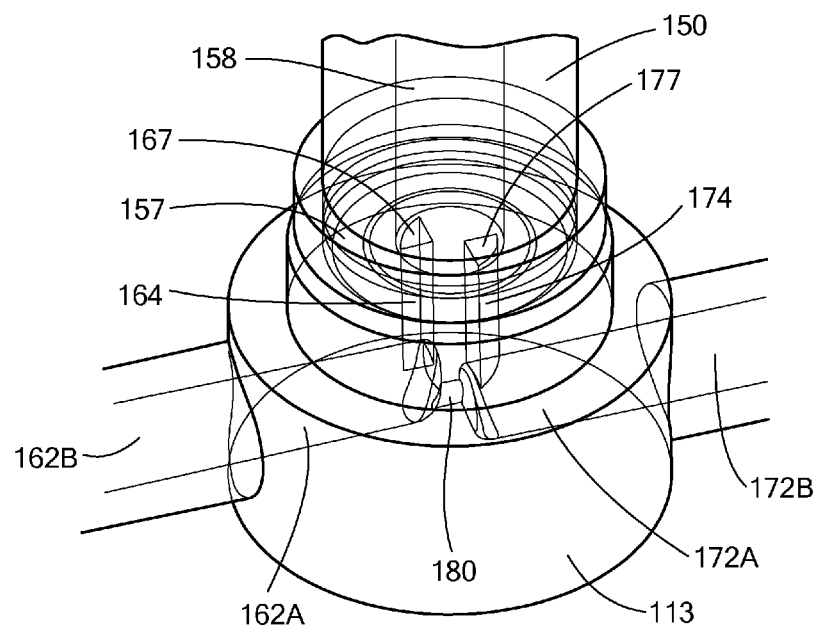
FIG. 13B schematically shows a detail view of the alternative sampling port shown in FIG. 13A in accordance with additional embodiments of the present invention.
Figure 13C:
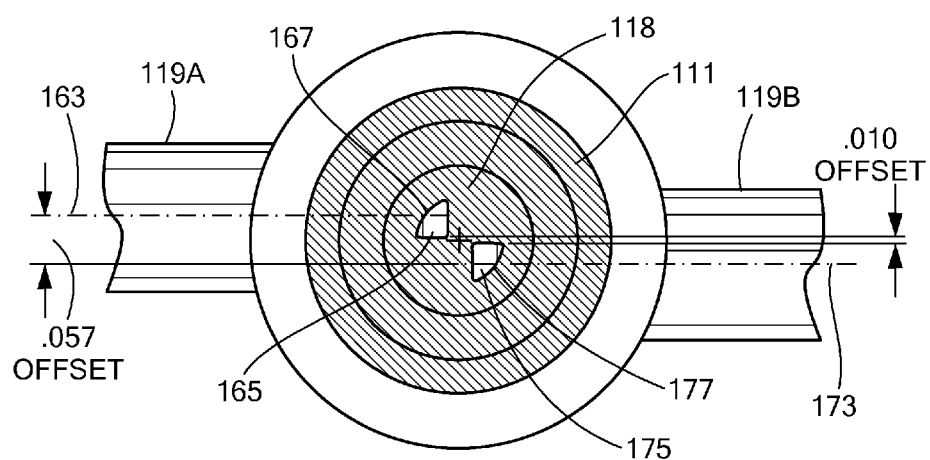
FIG. 13C schematically shows a top view of the alternative sampling port shown in FIG. 13A in accordance with additional embodiments of the present invention.

It is also important to note that the offset orientations discussed above can be varied based upon the desired application and use of the sampling port 100. For example, as shown in FIGS. 13A-13C, the offsets can be increased by increasing the distance between the first proximally extending axis 166 and the second proximally extending axis 176. As best shown in FIG. 13C, this can be accomplished by increasing the distance between the radial longitudinal axes 163/173 (e.g., by moving the inlet 120 and outlet 130 further off center).

Additionally or alternatively, the location of one or both of the proximally extending portions 164/174 can be moved relative to the radial longitudinal axes 163/173. For example, the proximally extending portions 164/174 can be located such that they are not aligned with the radial longitudinal axes 163/173. In other words, the first proximally extending portion 164 can be moved off the first radial longitudinal axis 163 in one direction (e.g., upwards from the perspective of FIG. 13C) and the second proximally extending portion 174 can be moved off the second radial longitudinal axis 173 in the opposite direction (e.g., downward from the perspective of FIG. 13C). In this manner, the spacing between the radial longitudinal axes 163/173 may remain the same, but the distance/offset between the proximally extending longitudinal axes 166/176 (and thus the proximally extending portions 164/174) is increased.

Figure 14A:
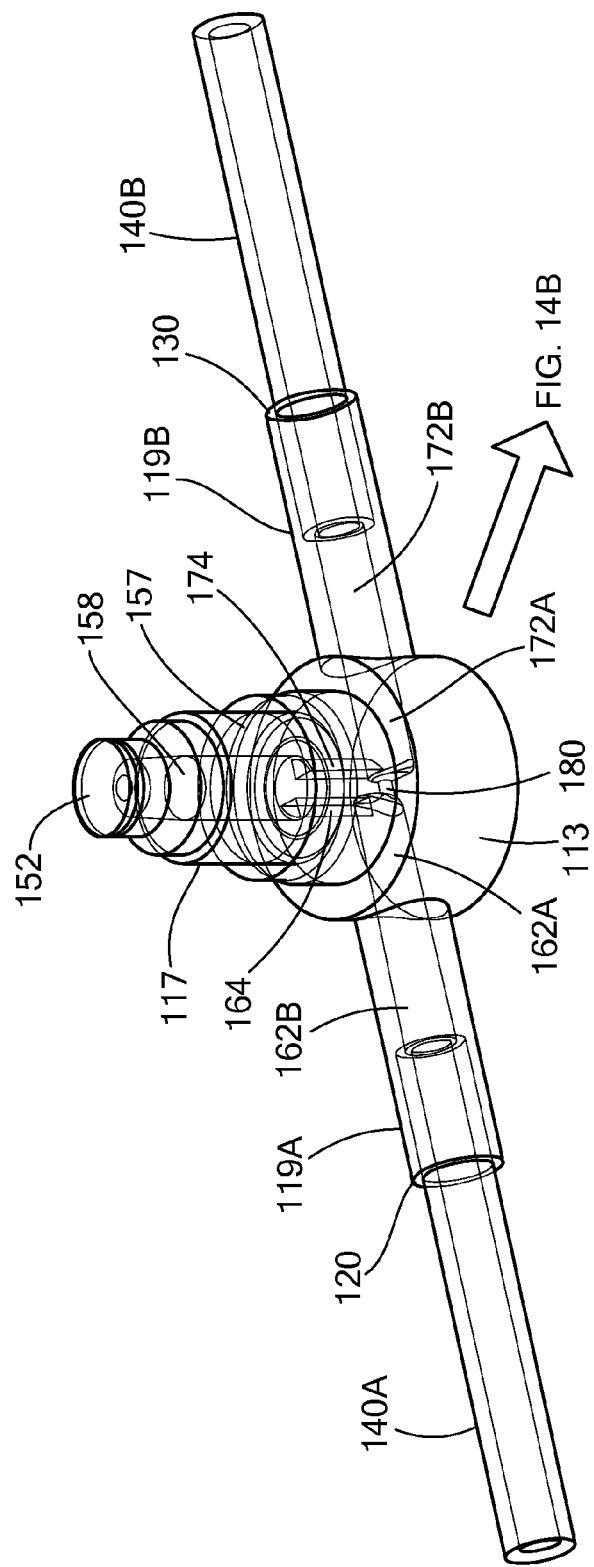
FIG. 14A schematically shows a perspective view of an additional alternative sampling port with the proximal portion of the hub removed in accordance with some embodiments of the present invention.
Figure 14B:
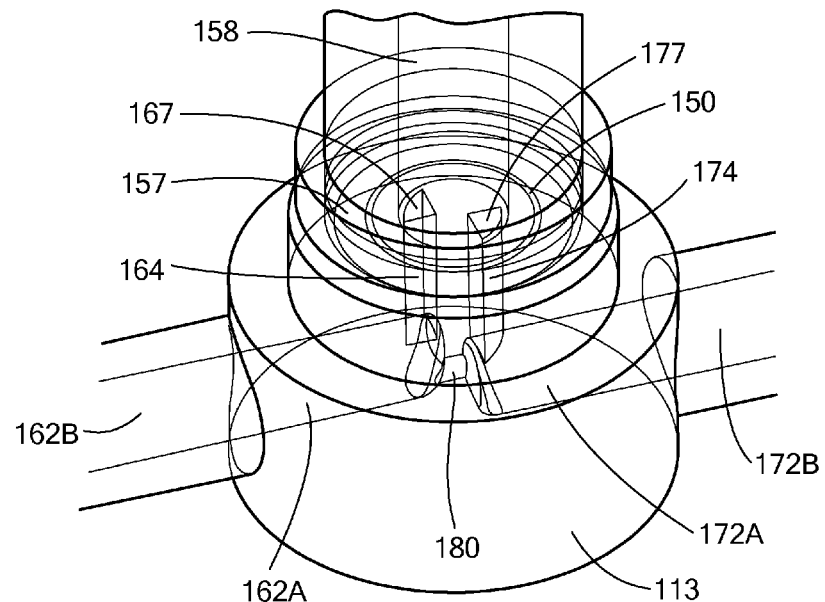
FIG. 14B schematically shows a detail view of the additional alternative sampling port shown in FIG. 14A in accordance with some embodiments of the present invention.
Figure 14C:
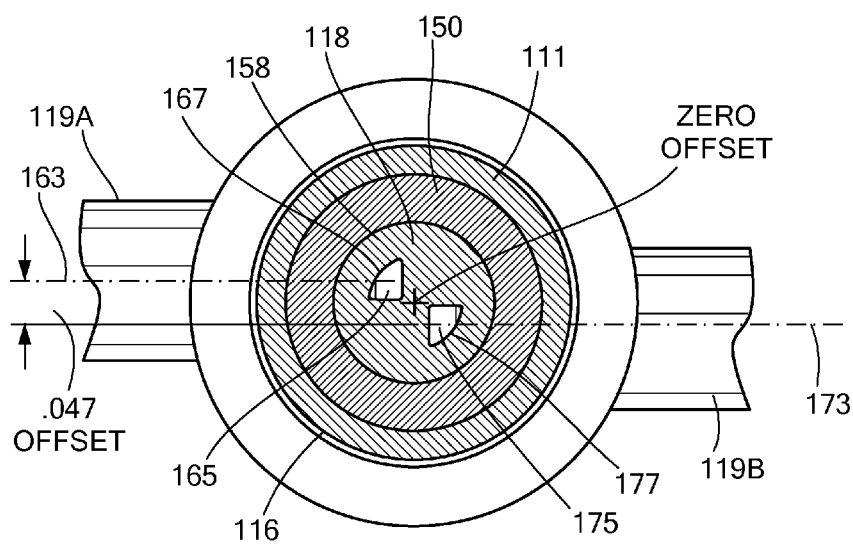
FIG. 14C schematically shows a top view of the additional alternative sampling port shown in FIG. 14A in accordance with some embodiments of the present invention.

Conversely, in some instances, it may be desirable to decrease the offset (FIGS. 14A-14C). For example, the offset may be decreased by decreasing the distance between the first proximally extending axis 166 and the second proximally extending axis 176. Additionally or alternatively, the offset may be decreased by altering the location of the proximally extending portions 164/174 with respect to the radial longitudinal axes 163/173 (e.g., such that they are closer together).

Figure 15A:
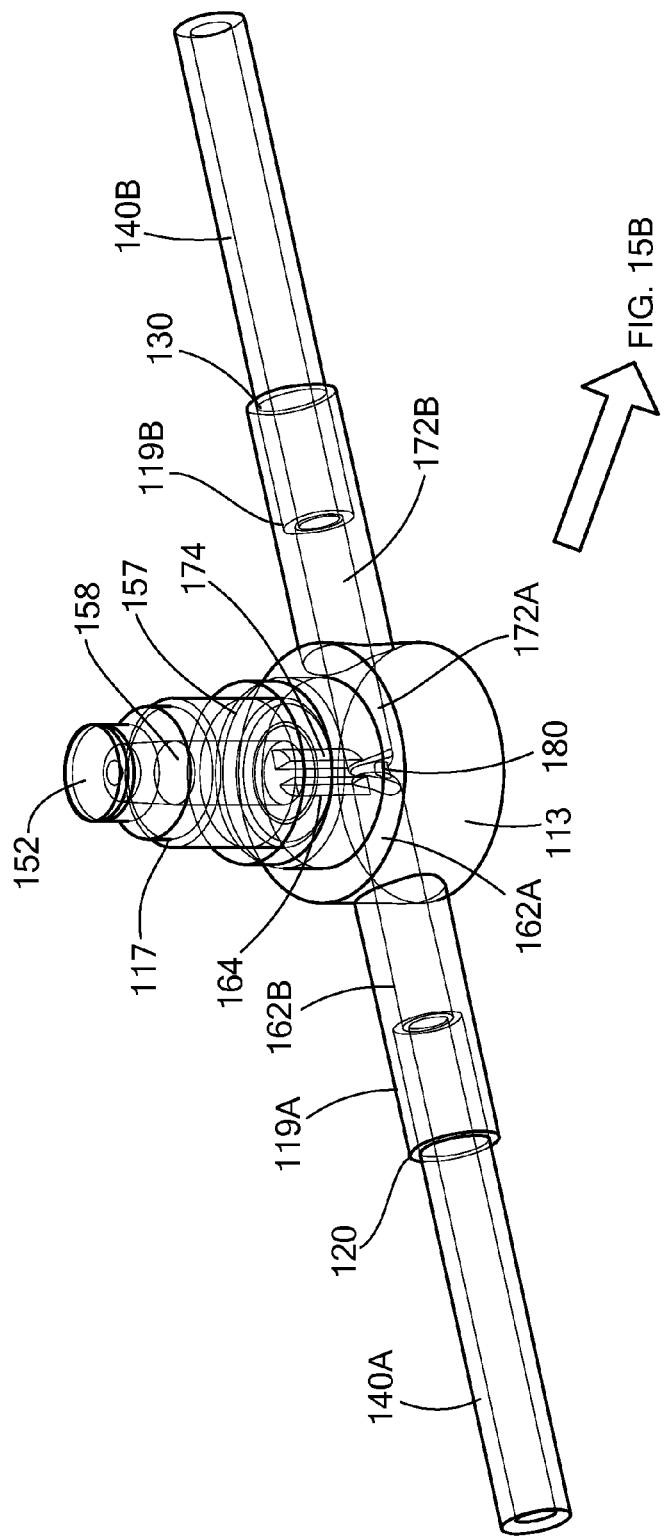
FIG. 15A schematically shows a perspective view of a further alternative sampling port with the proximal portion of the hub removed in accordance with additional embodiments of the present invention.
Figure 15B:
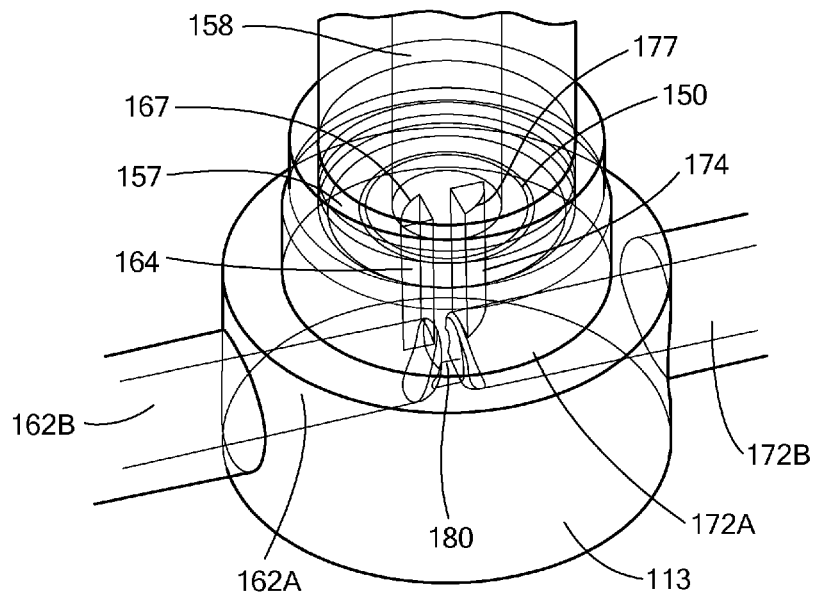
FIG. 15B schematically shows a detail view of the further alternative sampling port shown in FIG. 15A in accordance with additional embodiments of the present invention.
Figure 15C:
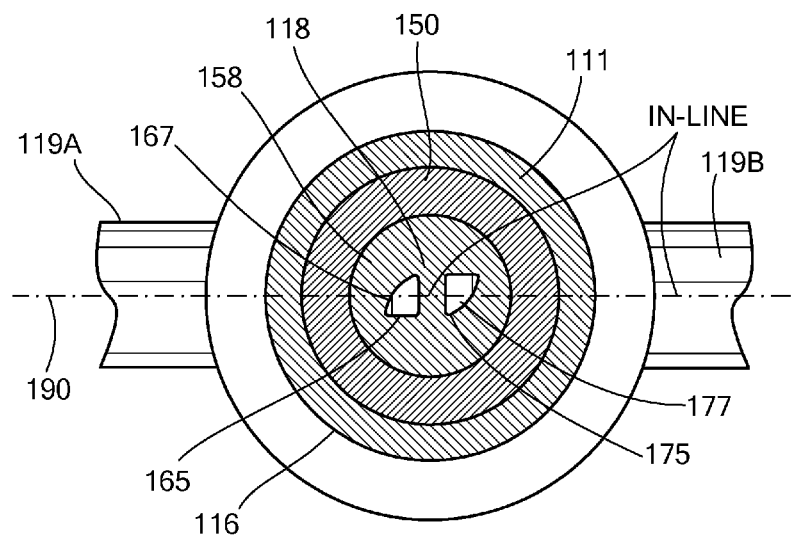
FIG. 15C schematically shows a top view of the further alternative sampling port shown in FIG. 15A in accordance with additional embodiments of the present invention.

Furthermore, in some embodiments, it may be desirable not to have any offset (FIGS. 15A-15C). In such embodiments, the first and second fluid channels 160/170 can be positioned such that the radial portions 162/172 are coaxial (e.g., they share the same radial longitudinal axis). Furthermore, if the proximally extending portions 164/174 are both aligned with the radial longitudinal axes 163/173, then the radial portions 162/172, the inlet 120 and outlet 130, and the proximally extending portions 164/174 will not be offset (e.g., they will all be aligned along a single longitudinal axis 190).

It should be understood that the various embodiments of the sampling port 100 described above provide numerous advantages over prior art sampling ports. Among others, under expected fluid flow rates such as while the transfer set is being flushed with fluid from a fluid bag, the design urges more fluid proximally to more fully flush the interior of the valve interior 158. This improved flushing is accomplished without the need for the practitioner to manipulate or otherwise move the sample port 100—it thus may be considered to be "self-flushing." This is in contrast to prior art stop-cock designs, which require rotational manipulation of the various flow paths with their systems. Illustrative embodiments therefore are free of stop-cock valves, rendering their flow paths through the sample port 100 generally stationary relative to the outer body. Further, the sampling port 100 ensures that the fluid transfer set is not inappropriately under/over dampened during use (e.g., the presence of the sampling port 100 does not negatively interfere with the pressure monitoring when a sample is not being taken).

Although the above discussion discloses various exemplary embodiments of the invention, it should be apparent that those skilled in the art can make various modifications that will achieve some of the advantages of the invention without departing from the true scope of the invention.

What is claimed is:

1. A sampling port comprising:
   a hub having a body forming a hub chamber for containing a fluid, the hub further having a proximal opening to the hub chamber for receiving a medical implement, the hub chamber having a valve member normally closing the opening, the valve member having a valve wall forming a valve interior;
   a first fluid channel formed by the hub body, the first fluid channel being in fluid communication with the hub chamber, the first fluid channel having a first radial portion having a first radial longitudinal axis and a first proximally extending portion having a first proximally extending flow path with a first proximally extending longitudinal axis; and
   a second fluid channel formed by the hub body, the second fluid channel being in fluid communication with the hub chamber, the second fluid channel having a second radial portion having a second radial longitudinal axis and a second proximally extending portion having a second proximally extending flow path with a second proximally extending longitudinal axis,
   the first and second proximally extending longitudinal axes forming a plane therebetween that diverges from the first radial longitudinal axis, such that no face of the plane is parallel with the first radial longitudinal axis and the second radial longitudinal axis.

2. The sampling port as defined by claim 1 wherein the first proximally extending flow path has a first cross-sectional shape, the second proximally extending flow path having a second cross-sectional shape, the first and second cross-sectional shapes being the same.

3. The sampling port as defined by claim 2 wherein the first cross sectional shape is oriented about 180 degrees relative to the second cross-sectional shape.

4. The sampling port as defined by claim 1 wherein the first proximally extending flow path is aligned with and generally orthogonal to the first radial longitudinal axis.

5. The sampling port as defined by claim 1 wherein the first and second proximally extending portions extend into the valve interior.

6. The sampling port as defined by claim 1 wherein the first radial longitudinal axis is generally parallel with and spaced from the second radial longitudinal axis.

7. The sampling port as defined by claim 1 wherein the first radial longitudinal axis and second radial longitudinal axis diverge.

8. The sampling port as defined by claim 1 wherein the valve wall forms a distal port for the valve interior, the first proximally extending portion having a proximally facing port, the distal port being more proximal than the proximally facing port or the distal port sharing the same plane as the proximally facing port.

9. The sampling port as defined by claim 1 wherein the first and second proximally extending portions are completely unmovable relative to the hub.

10. The sampling port as defined by claim 1 wherein the hub body comprises a distal portion, the hub chamber being proximal to the distal portion, the distal portion forming the first proximally extending portion and the second proximally extending portion, the first proximally extending portion terminating at a first proximally facing port, the second proximally extending portion terminating at a second proximally facing port, the first and second proximally facing ports terminating at the boundary of the hub chamber.

11. The sampling port as defined by claim 1 further comprising a bypass channel with a bypass longitudinal axis, the bypass channel directly fluidly connecting the first radial portion and the second radial portion, the bypass longitudinal axis being substantially parallel with the first radial longitudinal axis, the second radial longitudinal axis, or both the first and second radial longitudinal axes.

12. The sampling port as defined by claim 1 wherein the valve member comprises an elastomeric member having a proximal, swabbable portion.

13. The sampling port as defined by claim 1, wherein the second radial longitudinal axis is parallel to the first radial longitudinal axis.

14. A sampling port comprising:
   a hub having a body forming a hub chamber for containing a fluid, the hub further having a proximal opening to the hub chamber for receiving a medical implement, the hub chamber having a valve member normally closing the opening;
   a first fluid channel formed by the hub body, the first fluid channel being in fluid communication with the hub chamber, the first fluid channel having a first radial portion and a first proximally extending portion, the first radial portion having a first longitudinal axis; and
   a second fluid channel formed by the hub body, the second fluid channel being in fluid communication with the hub chamber, the second fluid channel having a second radial portion and a second proximally extending portion, the second radial portion having a second longitudinal axis,
   the first longitudinal axis being generally parallel with and laterally spaced from the second longitudinal axis such that the first and second longitudinal axes at least partially define a plane that is generally parallel to and located distally from the proximal opening to the hub chamber.

15. The sampling port as defined by claim 14 wherein the first proximally extending portion is substantially orthogonal to the first longitudinal axis.

16. The sampling port as defined by claim 15 wherein the second proximally extending portion is substantially orthogonal to the second longitudinal axis.

17. The sampling port as defined by claim 14 wherein the first proximally extending portion includes a first proximally facing fluid port.

18. The sampling port as defined by claim 17 wherein the second proximally extending portion includes a second proximally facing fluid port.

19. The sampling port as defined by claim 14 wherein the first proximally extending portion is spaced from the first longitudinal axis, the first proximally extending portion being aligned with the first longitudinal axis.

20. The sampling port as defined by claim 14 wherein the first and second proximally extending portions oppose each other at an angle to the first longitudinal axis.

21. The sampling port as defined by claim 14 wherein the valve member comprises an elastomeric member having a proximal, swabbable portion.

22. The sampling port as defined by claim 14 wherein the valve member comprises a normally closed proximal opening and a valve wall forming a valve interior, at least one of the first and second proximally extending portions extending into the valve interior.

23. The sampling port as defined by claim 14 wherein the valve member comprises a normally closed proximal opening and a valve wall forming a valve interior, at least one of the first and second proximally extending portions having a proximally facing port configured to direct fluid into the valve interior.

24. The sampling port as defined by claim 14 wherein the first radial portion includes a first interior radial portion within the hub chamber and a first exterior radial portion outside of the hub chamber.

25. The sampling port as defined by claim 14 further comprising a bypass channel with a bypass longitudinal axis, the bypass channel directly fluidly connecting the first radial portion and the second radial portion, the bypass longitudinal axis being substantially parallel with the first longitudinal axis, the second longitudinal axis, or both the first and second longitudinal axes.

26. The sampling port as defined by claim 25 wherein the bypass longitudinal axis is spaced from the first longitudinal axis.

* * * * *